United States Patent [19]

Tiebor et al.

[11] 4,317,997

[45] Mar. 2, 1982

[54] POSITIONING FIXTURE FOR MEASURING INSTRUMENTS

[75] Inventors: John E. Tiebor, Williamsville; Jerry J. Spongr, Tonawanda; Ralph J. Dalfonso, Alden, all of N.Y.

[73] Assignee: Twin City International, Inc., Amherst, N.Y.

[21] Appl. No.: 151,785

[22] Filed: May 21, 1980

[51] Int. Cl.³ .............................................. G01N 23/00
[52] U.S. Cl. ...................................... 250/308; 250/491
[58] Field of Search ........................ 250/308, 491, 505

[56] References Cited

U.S. PATENT DOCUMENTS 2,759,108 8/1956 Molins .................................. 250/308
3,115,577 12/1963 Joffe et al. ........................... 250/308

Primary Examiner—Bruce C. Anderson
Attorney, Agent, or Firm—Christel, Bean & Linihan

[57] ABSTRACT

A component positioning fixture is provided for use with a beta backscatter measuring platen having an apertured seat. The fixture has a plate with an opening therethrough for the apertured seat, and alinement pins properly position the plate on the platen. At least one component positioning member is carried by the fixture plate, the member being selectively adjustable relative to the fixture opening for proper positioning of the component to be measured on the apertured seat of the platen. The positioning member is releasably secured in adjusted position and can include a stop member engageable by the component, a member shaped to receive and position the component and interchangeable with other members shaped to receive and position other components, and a pair of positioning guide members movable relative to each other and to the fixture opening along an axis which can be arranged normal to the axis of movement of the stop member. The component positioning member can be mounted for movement relative to the opening along a first axis, and in opposite directions laterally of that axis.

9 Claims, 10 Drawing Figures

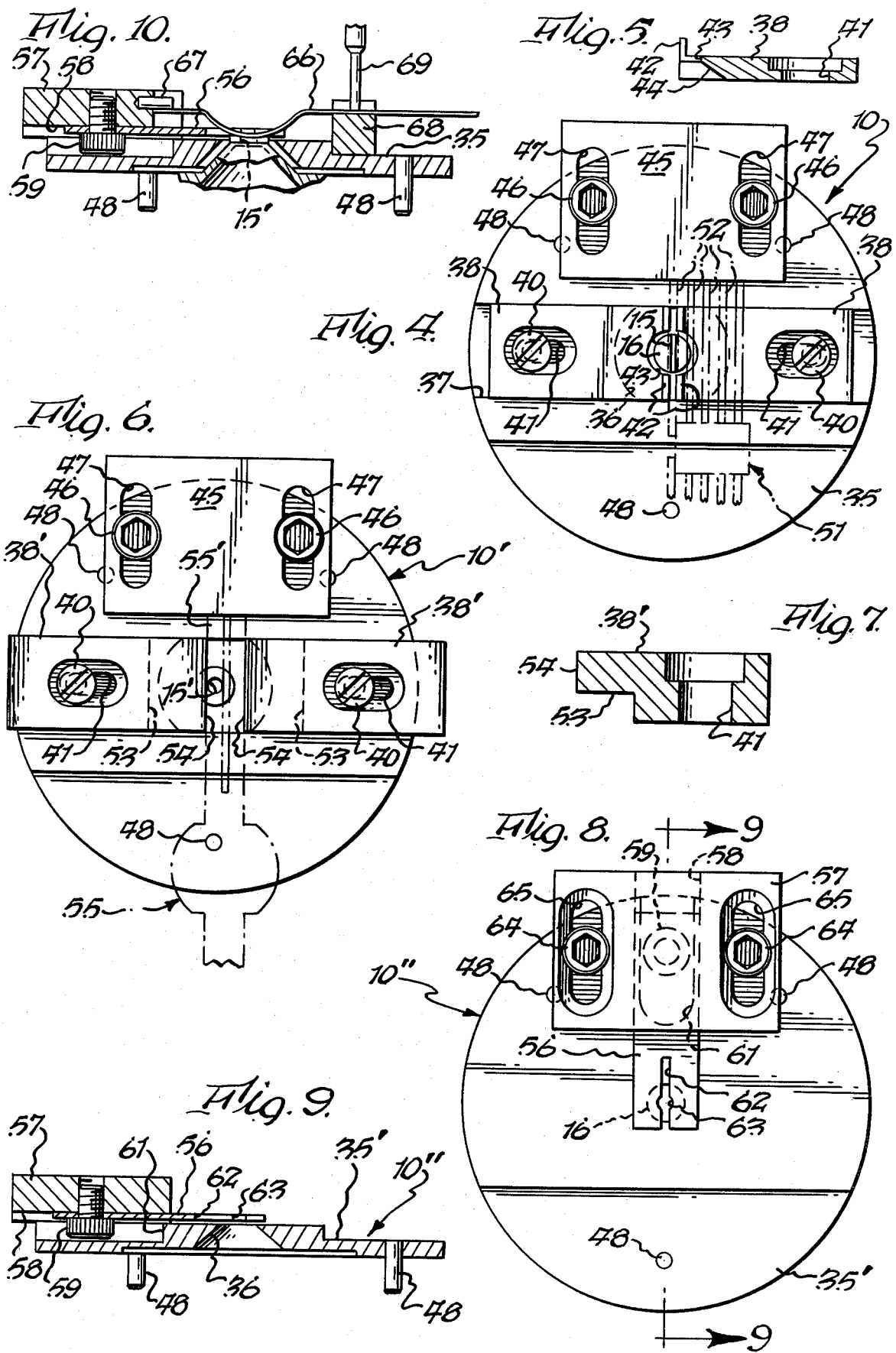

POSITIONING FIXTURE FOR MEASURING INSTRUMENTS

BACKGROUND OF THE INVENTION

This invention relates to positioning fixtures useful with measuring platens in systems using radiation techniques for measurement of ultra thin coatings and the like, and particularly beta backscatter measuring systems such as described, for example, in U.S. Pat. No. 3,132,248 dated May 5, 1964.

In such systems it is important that the component area being measured be carefully delimited, and for that purpose it is known to provide interchangeable platens having exposure apertures of different sizes and configurations, thereby permitting the system to be used with an aperture best suited to the component being measured. Such interchangeable platens are shown, for example, in U.S. Pat. No. 3,115,577 dated Dec. 24, 1963.

Even with appropriately shaped and sized apertures, the positioning of small parts can be difficult and time consuming, particularly where repeatability in positioning is important. It is known to provide a fixture which is shaped to receive a particular part, for use with the aperture plate or platen to facilitate the positioning of successive identical parts. To measure a differently shaped or sized part, a different positioning fixture is provided. This requires a multiplicity of fixtures.

SUMMARY OF THE INVENTION

The primary object of this invention is to provide a measuring platen component positioning fixture which is adjustable to accommodate a variety of components of different shapes and sizes.

Another object of this invention is to provide the foregoing in a fixture which is simple in construction, durable and dependable in operation, quickly and easily adjusted to accommodate a wide variety of components to be measured, and which is relatively inexpensive and highly suitable for the intended purpose.

The foregoing and other objects, advantages and characterizing features of this invention will become clearly apparent from the ensuing detailed description taken in conjunction with the accompanying drawings wherein like reference numerals denote like parts throughout the various views.

BRIEF DESCRIPTION OF THE DRAWING FIGURES

FIG. 4 is a top plan view of the positioning fixture, on a reduced scale, showing a component positioned thereby;

FIG. 5 is a vertical sectional view of one of the adjustable positioning guide members, taken on the same plane as line 2—2 of FIG. 1;

FIG. 6 is a top plan view of a positioning fixture of this invention incorporating a modified form of positioning guide member;

FIG. 7 is a view like that of FIG. 5, but showing the modified positioning guide member of FIG. 6;

FIG. 8 is a top plan view of still another positioning fixture of this invention;

FIG. 9 is a vertical sectional view thereof, taken about on line 9—9 of FIG. 8; and FIG. 10 is a view like that of FIG. 9, but illustrating still another modification of this invention.

DESCRIPTION OF THE ILLUSTRATED EMBODIMENTS

Referring first to the embodiment of FIGS. 1-5, a component positioning fixture of this invention, generally designated 10, is shown in conjunction with a platen generally designated 11. It will be appreciated that fixture 10 is not limited to use with platen 11, which has been selected only by way of illustration.

Figure 1:
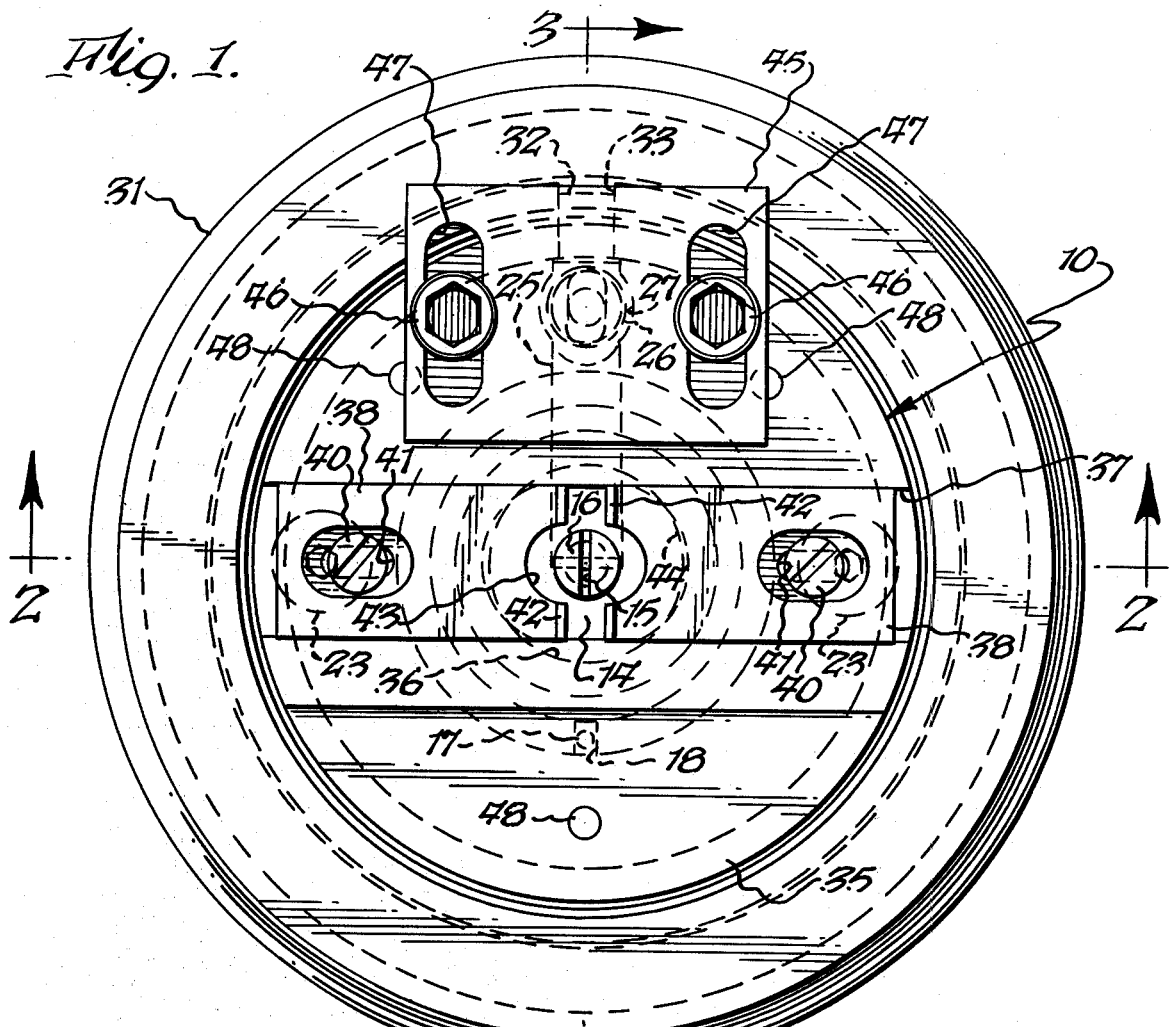
FIG. 1 is a top plan view of one form of positioning fixture of this invention, shown in place on a measuring platen.
Figure 2:
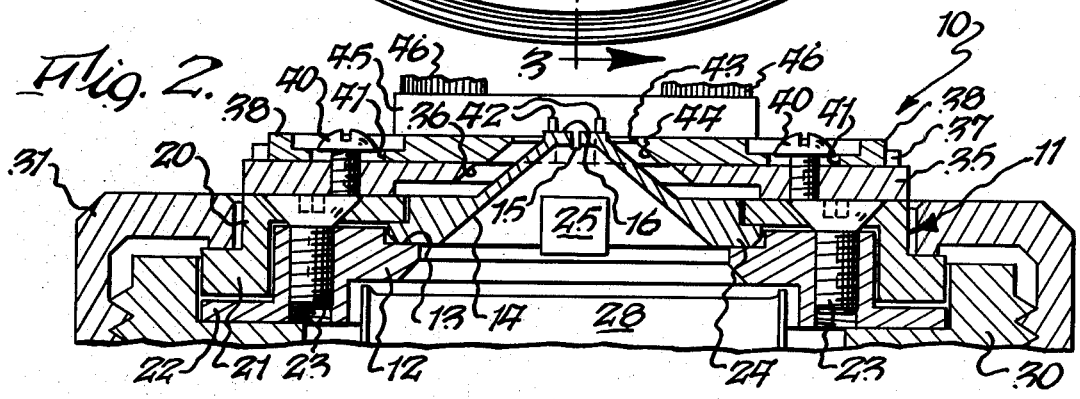
FIG. 2 is a vertical sectional view thereof, taken about on line 2—2 of FIG. 1, parts being broken away for convenience in illustration.
Figure 3:
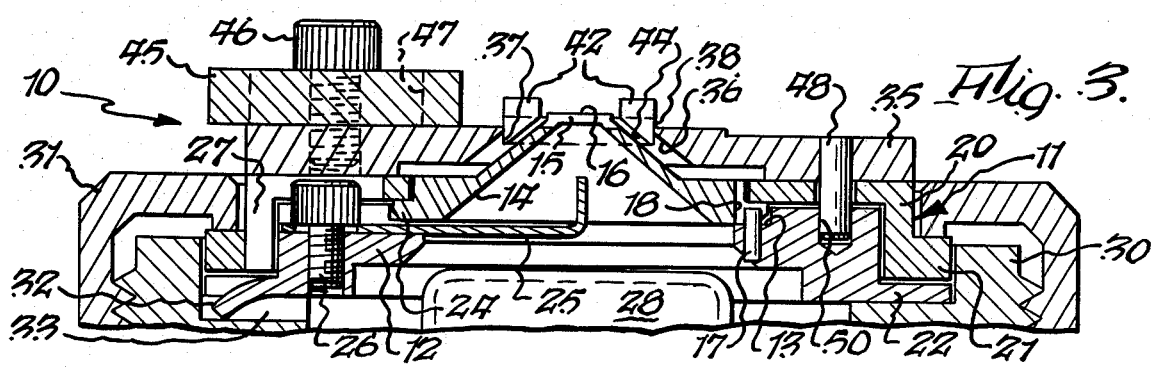
FIG. 3 is a vertical sectional view thereof taken about on line 3—3 of FIG. 1.

Looking first at platen 11 and associated parts other than the fixture 10, there is shown in FIGS. 2 and 3 a three part platen consisting of an annular base plate 12 having a stepped inner circumference providing an annular ledge 13, an interchangeable insert 14 of annular, frustoconical shape having a central aperture 15 through a flat seating surface 16, the aperture being shown as an elongated slot although other shapes and sizes of apertures could be provided. Insert 14 is positioned on ledge 13 in proper alinement in platen 11 by a pin 17 seated in base plate 12 and received in a groove or opening 18 in insert 14. The insert 14 is held in position in the platen by an annular top plate 20 having a depending skirt and laterally extending flange 21 at the lower end thereof, complimenting the shape of base plate 12 which also has a laterally projecting flange 22. Top plate 20 is secured to base plate 12 by screws 23, and extends partially over shoulder 13, overlying and bearing against an external flange 24 on insert 14 for holding the platen assembled. When changing inserts, to substitute another having an aperture of different shape or size, the screws 23 are removed, permitting removal of top plate 20 and substitution of another insert.

An isotope holder 25 is positioned on base plate 12 by a screw 26, the holder 25 being slotted to permit inward and outward adjustment of the holder. Top plate 20 is slotted or grooved, as shown at 27, to accommodate and permit access to the head of screw 26 and also to accommodate the outer end of isotope holder 25 if it is shifted to a position causing it to extend outwardly of base plate 12.

A radiation detector in the form of a Geiger-Muller (GM) tube is positioned in a suitable manner in a probe housing 30, and platen 11 is held in proper position in the probe by a ring 31 having threaded engagement with housing 30. An alinement tail 32 on platen base plate 12 engages a groove 33 in probe housing 30, to properly aline platen 11, insert 14 and GM tube 28.

As noted above, the three part platen 11 with self contained isotope is shown in the drawing by way of illustration only, and the usefulness of the positioning fixtures of this invention is not limited in any way to a particular platen.

Positioning fixture 10 includes a base plate 35 having a frustoconical central opening 36 sufficiently large to permit insert 14 to project through, positioning aperture seat 16 being above plate 35 to receive the component being measured. Plate 35 also is formed to provide a groove 37 extending across the plate, the center of the groove 37 lying on the diameter of plate 35 and opening 36. A pair of adjustable positioning guide members 38 is fitted in groove 37 for movement in opposite directions toward and away from each other and from opening 36. This is accomplished by screws 40 which fit through slots 41 in members 38, the slots being elongated along the axis of movement of members 38, and being recessed to accommodate the screw heads.

The adjacent ends of members 38 are formed with upstanding flanges 42 and are recessed as shown at 43 and generally conically shaped as shown at 44 to accommodate insert 14 and permit flanges 42 to be positioned closer together than the diameter of apertured seat 16, as shown in the drawing. Members 38 are adapted to receive a component to be measured between flanges 42, in a manner described hereafter.

Positioning fixture 10 also includes an adjustable stop member 45 positioned for movement toward and away from opening 36 along an axis at right angles to the axis of movement of members 38, and intersecting that axis at the center of the platen aperture. To this end, member 45 is positioned on the upper surface of base plate 35, being held thereon by screws 46 which extend through slots 47 in stop 45 into top plate 35. Slots 47 are elongated in directions parallel to the axis of movement of stop 45.

Stop member 45 is intended to act as an abutment for a component part fitted between members 38, and can be moved closer to or further from the aperture 15 by loosening screws 46, shifting stop 45 to the proper position, and then tightening the screws to secure stop 45 in adjusted position. Where the component being measured is extremely long, stop 45 can be removed from positioning fixture 10 by removing screws 46 and stop 45, permitting the component to extend across base plate 15 in the area normally occupied by the stop.

Positioning fixture 10 is provided with alinement pins 48 carried by base plate 35, and spaced apart around the base plate, depending therefrom for insertion through clearance openings in top plate 20 into alinement openings 50 in platen base plate 12. In this way positioning fixture 10 is precisely positioned and the various parts properly oriented relative to aperture 15.

Looking at FIG. 4, positioning fixture 10 is shown in use with a lead frame 51, for measuring the coating thickness of one of the leads 52 thereof. As shown, positioning guide members 38 are positioned to receive a lead 52 between them, in precise alinement with aperture 15, and stop 45 is positioned so that when the lead frame is placed on fixture 10 with the lead ends against stop 45 the precise portion of the lead to be measured engages seat 16 over aperture 15. Once the position of members 38 and 45 has been adjusted, frame 51 can be repositioned to place another of its leads 52 between the flanges 42, for measurement of its coating thickness, and the fixture will accurately position successive lead frames being tested. There is no need for the operator to do anything more than place the lead frame between the positioning guide members 38, and against stop 52, whereupon repeatability and accuracy are assured.

When a different component part is to be measured, the position of members 38 and of stop 45 is adjusted to receive and properly position such component, whatever it may be. The component part being measured may be positioned between the guide member flanges 42, as shown in FIG. 4. In other cases, the guide member flanges can be offset relative to the aperture, receiving another portion of the component under test in a manner positioning the portion to be measured in precise alinement with aperture 15.

This is illustrated in FIG. 6 which shows a positioning fixture generally designated 10'. Fixture 10' is like fixture 10 except that the positioning guide members 38' are slightly modified, those parts which are the same being numbered the same. In the embodiment of FIGS. 6 and 7, positioning guide members 38' are undercut, as shown at 53, to permit their ends 54 to overhang the base plate opening and also insert 14 and apertured seat 16. In this instance, the aperture 15' is circular. FIG. 6 shows a bifurcated contact 55 under test, with one of the bifurcated contact elements 55' being measured. Therefore, both elements 55' are positioned between end faces 54 which are adjusted to be off center, relative to aperture 15'. When contact 55 is positioned between end faces 54, and against stop 45, one of the elements 55' will be properly seated over and against aperture 15', for test.

Another form of positioning fixture of this invention, generally designated 10'', is illustrated in FIGS. 8 and 9. In this form, base plate 35' has a central opening 36 shaped to accommodate insert 14. A positioning guide member 56 is carried by a mounting member 57, fitting in a groove 58 in the undersurface thereof and being secured thereto by a screw 59. Base plate 35' is grooved at 61 to accommodate the head of screw 59.

Member 56 is shaped to receive and position a component to be measured, being inwardly slotted at 62, providing a bifurcated end portion which has a circular opening 63 intended to be positioned in alinement with the opening 36 and the aperture 15 or 15' of platen insert 14. Mounting member 57 is secured to fixture plate 35' by screws 64 extending through slots 65 which are parallel to each other and to member 56. Loosening screws 64 permits mounting member 57 to be shifted along an axis lying on the diameter of plate 35', intersecting the center of its opening 36 and the insert aperture therebeneath. In addition, the relative size of slots 65 and screws 64 is such as to permit a limited amount of play and rotation, to move member 56 laterally in opposite directions relative to the axis through the fixture opening. Therefore, with this arrangement positioning member 56 is capable of rectilinear movement and also a limited degree of lateral shifting or swinging movement in opposite directions.

FIG. 10 shows still another arrangement in which stop 45 (or mounting member 57) has a grooved end face receiving the end of a component 66. A hold-down pin 67 is provided in the grooved end face. A bearing block 68 is positioned on the fixture base plate 35 (or 35') and shaped to receive a section of the component 66 spaced from the end which engages stop 45. With this arrangement, component 66 is positioned between members 38 or 38', or in member 56, as the case may be, with its end engaged beneath pin 67. The component can be held in position on block 68 by a pressure pin 69. Such pressure pins are well known in this art, and in conjunction with pin 67 and the other elements of the positioning fixture maintains component 66 in proper position against aperture 15' for accurate measurement.

Accordingly, it is seen that this invention fully accomplishes its intended objects, providing a positioning fixture which is adjustable to accommodate a wide variety of components to be measured and which can accommodate component positioning parts of different types and configurations. The positioning fixture is precisely alined with the platen, in a manner such that the apertured insert seat projects above the fixture base plate, through an opening therein, to permit proper seating of the component portion to be measured. While selected embodiments have been disclosed and described herein, it will be appreciated that this has been done by way of illustration only, and not by way of limitation.

What is claimed is:

1. A component positioning fixture for use with a measuring system utilizing radiation and having a platen with an apertured seat for receiving the component being measured, said fixture comprising a base plate having an opening therethrough for the apertured seat of the platen, means for both radially and circumferentially alining said base plate with the platen, at least one component positioning member carried by said base plate, said positioning member being selectively laterally adjustable along a first axis substantially perpendicular to the axis of said opening for proper positioning of a component to be measured on the apertured seat of the platen, and means for releasably securing said positioning member in adjusted position.

2. A component positioning fixture as set forth in claim 1, together with pair of positioning guide members movable relative to each other and to said opening along a second axis normal to said first axis.

3. A component positioning fixture as set forth in claim 1, said positioning member being movable in opposite directions relative to said opening along a first axis, said member also being movable relative to said opening in opposite directions laterally of said first axis.

4. A component positioning fixture as set forth in claim 1, having a pair of component positioning members movable relative to each other and to said opening along a first axis.

5. A component positioning fixture as set forth in claim 4, for use with a platen having an apertured insert adapted to project through said opening, the adjacent ends of said members being recessed to accommodate the platen insert.

6. A component positioning fixture as set forth in claim 1, wherein said component positioning member includes a portion shaped to receive and position a component to be measured, a mounting member, said mounting member being selectively adjustable for movement relative to said opening and being releasably secured in adjusted position, means releasably securing said positioning member to said mounting member for movement therewith and for replacement by an interchangeable positioning member shaped to receive and position a different component to be measured.

7. A component positioning fixture as set forth in claim 1, said stop having hold-down means for engagement with an end portion of a component to be measured.

8. A component positioning fixture as set forth in claim 7, together with bearing block means carried by said fixture plate on the side of said opening opposite said stop, said bearing block means being shaped for seating engagement with another portion of a component to be measured.

9. A component positioning fixture as set forth in claim 1, in combination with a platen having a top plate and an interchangeable insert providing an apertured seat for a component to be measured, said fixture base plate and said platen top plate having alinement pins and pin receiving openings coacting to position said fixture on said platen with said insert projecting through said opening.

* * * * *